United States Patent [19]

Kurek

[11] Patent Number: 5,126,489
[45] Date of Patent: Jun. 30, 1992

[54] ACYLATION OF AROMATIC COMPOUNDS BY ACID ANHYDRIDES USING SOLID ACID CATALYSTS

[75] Inventor: Paul R. Kurek, Barrington, Ill.

[73] Assignee: UOP, Des Plaines, Ill.

[21] Appl. No.: 696,385

[22] Filed: May 6, 1991

[51] Int. Cl.$^5$ .............................................. C07C 45/45
[52] U.S. Cl. .................................................... 568/319
[58] Field of Search ......................................... 568/319

[56] References Cited

U.S. PATENT DOCUMENTS

| | | | |
|---|---|---|---|
| 3,965,043 | 6/1976 | Stridde | 252/455 R |
| 3,979,331 | 9/1976 | Stridde | 252/441 |
| 4,304,941 | 12/1981 | Lee et al. | 568/319 |
| 4,406,821 | 9/1983 | Farcasiu | 252/440 |
| 4,459,234 | 7/1984 | Kawamata et al. | 260/369 |
| 4,499,319 | 2/1985 | Ballantine et al. | 585/467 |
| 4,605,806 | 8/1986 | Ballantine et al. | 585/467 |
| 4,652,683 | 3/1987 | Nicolau et al. | 568/319 |
| 4,714,781 | 12/1987 | Gupta | 568/319 |
| 4,754,074 | 6/1988 | Hussmann | 568/319 |
| 4,956,519 | 9/1990 | Hollstein et al. | 585/751 |
| 4,960,943 | 10/1990 | Botta et al. | 568/319 |
| 5,008,233 | 4/1991 | Lambert . | |

FOREIGN PATENT DOCUMENTS

| | | | |
|---|---|---|---|
| 51-001710 | 1/1976 | Japan . | |
| 60-25541 | 2/1985 | Japan | 568/319 |
| 64-245854 | 10/1989 | Japan . | |

OTHER PUBLICATIONS

Cornelis et al., Catalysis Letters, 6, 103-10 (1990).

Primary Examiner—James H. Reamer
Attorney, Agent, or Firm—Thomas K. McBride; Eugene I. Snyder

[57] ABSTRACT

Acylatable aromatic hydrocarbons may be acylated with a broad variety of carboxylic acid anhydrides in the presence of solid acid catalysts which replace conventional Friedel-Crafts catalysts to afford aromatic ketones in good yield and with high selectivity. Both aromatic and aliphatic carboxylic acid anhydrides may be used as the acylating agent, and solid acid catalysts such as the sulfated oxides of zirconia, pillared clays, and rare earth-exchanged pillared clays are found to be quite effective in the practice of this invention. The process may be practiced in a continuous mode, especially where excess aromatic compound is used as a reactant and is recycled from the product effluent to the reaction zone containing a bed of catalyst.

24 Claims, No Drawings

ACYLATION OF AROMATIC COMPOUNDS BY ACID ANHYDRIDES USING SOLID ACID CATALYSTS

BACKGROUND OF THE INVENTION

Both diaryl ketones and alkyl aryl ketones long have been staples of commerce with a wide variety of uses, both in end applications and as valuable intermediates in numerous chemical syntheses. Using benzophenone as an example which is an important subject of this application, the ketone and its substitutes have found use as photoinitiators for ultraviolet-curable printing inks and coatings as well as an ultraviolet stabilizer in plastics. It is employed in the perfume industry as a fixative and as a fragrance with a flowery note, and as an intermediate is used both in the pharmaceutical and agricultural chemical industries.

Benzophenone is usually produced by atmospheric oxidation of diphenyl methane in the presence of metal catalysts. Commercial production also can be effected by Friedel-Crafts acylation of benzene with benzyl chloride or of benzene with phosgene.

Friedel-Crafts acylation of aromatics to afford both diaryl and aryl alkyl ketones is a time honored method of preparation affording a broad chemical spectrum of ketones. Acid halides are the most prevalent acylating agents, most likely because of their high reactivity in the acylation of aromatic compounds. One unfortunate adverse use of acid halides as the acylating agent is the formation of the corresponding hydrogen halide as a reaction product. Since acid chlorides are by far the most commonly employed acid halide, hydrogen chloride is the hydrogen halide normally formed and, as is well known, is a highly acidic, corrosive material whether as a gas or in solution. Formation of such a corrosive acid is a major detriment in Friedel-Crafts acylation and is desirably to be avoided wherever this is feasible.

Even though a broad spectrum of Friedel-Crafts catalysts are known, aluminum chloride is the archetype because of its activity and near universal applicability as well as for its relative availability and low cost. However, aluminum chloride is not without its own problems. For example, it is extremely sensitive to moisture which causes formation of hydrogen chloride. Although it can be used as a solid acidic catalyst in a continuous process, its flow characteristics are far from desirable. Not the least of its disadvantages is the difficult problem associated with disposal of spent catalyst; because it is corrosive and difficult to handle, aluminum chloride poses somewhat of an environmental hazard. That all these difficulties can be dealt with is clear from the fact it has been used as a Friedel-Crafts catalyst for many decades.

In the course of investigating preparative methods for benzophenone, the various oxidative methods quickly proved disadvantageous. Just as quickly it became clear that Friedel-Crafts acylation would be most desirable so long as certain attributes could be incorporated into a procedure. In particular, it became apparent that acid halides were undesirable acylating agents and that aluminum chloride, and similar materials used as Friedel-Crafts catalyst, were not acceptable. Although acid anhydrides long have been used as an acylating agent, they often are disfavored both because of their low reactivity relative to acid halides and because only one of the acid residues is incorporated as a carbonyl group into the ketone, with the other acid residue merely regenerating the carboxylic acid. Since the acid anhydride generally is made from the acid, it can be seen that the use of acid anhydrides is in some sense an inefficient utilization of the acid from which the anhydride is prepared.

Although a solid catalyst was desirable in order that a continuous process for the preparation of diaryl and aryl alkyl ketones could be designed, it was equally apparent that aluminum chloride, and materials similar to it, simply were not acceptable catalysts. Consequently it was necessary to find solid acidic catalysts that would function well in the acylation of aromatic compounds and which could be used in a continuous process for ketone preparation.

Some solid acidic catalysts already have been noted as acceptable substitutes for aluminum chloride, at least in particular acylation reactions. For example, Kawamata et al. U.S. Pat. No. 4,459,234 teach the preparation of anthraquinone in the vapor phase reaction of phthalic anhydride with benzene in the presence of a titanium or tin oxide catalyst. At high mole ratios of benzene to phthalic acid and at temperatures on the order of 500° C. the patentees observed over 90% conversion of phthalic acid with a selectivity to anthraquinone on the order of 80%. Somewhat analogous is JP76001710 which describes the preparation of anthraquinone from phthalic anhydride and benzene in the gas phase using group I metal aluminosilicates of the faujasite type as a catalyst. GB1499276 describes the vapor phase acylation of, for example, benzene and xylene at 250°-500° C. in the presence of certain silica-alumina catalysts.

What we have observed, and what forms the basis for the invention as claimed herein, is the reaction of aromatics, and especially aromatic hydrocarbons, with acid anhydrides, and especially aromatic carboxylic acid anhydrides, in the liquid phase at temperatures generally under 350° C. using a variety of solid acidic catalysts, including certain clays and sulfated metal oxides having extremely high acidity. Recently Cornelis et al., *Catalysis Letters*, 6, 103-10 (1990), have reported that various metal-impregnated and metal cation-exchanged clays are effective catalysts in liquid phase Friedel-Crafts acylation at temperatures on the order of 150° C. Although most acylations were performed using acid chlorides, the particularly reactive substrate anisole was acylated quantitatively at 160° C. using benzoic anhydride as the acylating agent. Kaolin, montmorillonite, and an otherwise unidentified "Japanese acidic" clay were the only ones reported.

SUMMARY OF THE INVENTION

The object of this invention is to prepare ketones by acylation of aromatic compounds with carboxylic acid anhydride using non-conventional solid acid catalysts as Friedel-Crafts catalysts. An embodiment of this invention comprises the reaction of an aromatic compound with a carboxylic acid anhydride in the presence of catalysts such as silicon-enhanced silica-aluminas, pillared clays, metal-exchanged pillared clays, and sulfated oxides of metals such as tungsten, zirconium, and titanium. In a more specific embodiment the catalyst is a sulfated oxide of zirconium. In another specific embodiment the carboxylic acid of the anhydride is an aromatic carboxylic acid. In another specific embodiment the aromatic compound is benzene or an alkyl substituted benzene. Yet another embodiment is a method of continuously preparing a ketone by reacting the aromatic compound with the carboxylic acid anhydride using a bed of a solid acid catalyst, collecting the product mixture from the reaction zone, separating the unreacted aromatic compounds at least from the formed ketone, and returning the separated aromatic compound to the reaction zone. Other embodiments will be apparent from the ensuing discussion.

DESCRIPTION OF THE INVENTION

As previously stated, it is desirable to obviate the use both of acid chlorides and of Friedel-Crafts catalysts such as aluminum chloride in the acylation of aromatic compounds to afford ketones. We have achieved this goal in totality using carboxylic acid anhydrides as the acylating agent and certain solid acid catalysts as a substitute for more conventional Friedel-Crafts catalysts. We have found that the solid acid catalysts of our invention effect acylation using carboxylic acid anhydrides under moderate acylation conditions to permit liquid phase reaction which affords the desired ketone in both good yield and good selectivity. The method is susceptible to great diversity in both the aromatic compound which is acylated as well as the carboxylic acid which may be used in the anhydride and thereby affords a very convenient and cost effective alternative to aromatic ketone preparation.

The aromatic compounds which may be used in the practice of this invention are acylatable aromatic compounds which include both simple, unsubstituted aromatics as well as many kinds of substituted aromatics. For example, among the unsubstituted aromatics may be mentioned benzene and its fused ring counterparts such as naphthalene, anthracene, phenanthrene, chrysene, and so forth. Among the substituted aromatic hydrocarbons which may be used are the alkyl substituted hydrocarbons. The alkyl groups may contain from 1 up to about 20 carbon atoms and include such groups as methyl, ethyl, propyl, butyl, pentyl, hexyl, heptyl, octyl, nonyl, decyl, undecyl, dodecyl, tridecyl, tetradecyl, and so forth. Although the monoalkyl-substituted aromatics are the most commonly used members of this group, polyalkyl-substituted aromatics also may be used. As a practical matter, Friedel-Crafts acylation often becomes unacceptably slow, because of steric effects, when more than 3 alkyl groups are present on the aromatic rings, and often are too slow to be of commercial interest with only 2 alkyl groups substituted on the aromatic rings. Consequently, although aromatic hydrocarbons containing up to 3 alkyl groups on the aromatic ring, each of which may contain from 1 up to about 10 carbon atoms, can in principle be used in the practice of this invention, those aromatic hydrocarbons containing either 1 or 2 alkyl groups as substituents on the aromatic ring, each of which contains from 1 to 6 carbon atoms, are more commonly employed.

The aromatic hydrocarbons also may bear one or more substituents in the aromatic ring which do not interfere with, or appreciably reduce the rate of, acylation. Such substituents include hydroxyl groups, alkoxy groups containing from 1 up to about 10 carbon atoms, and the halogens, especially chlorine and bromine. Examples of such materials include phenol, cresol, resorcinol, anisole, ethoxynaphthalene, chlorobenzene, dichlorobenzene, bromobenzene, chloroanthracene, propoxyethylbenzene, and so forth. As previously noted, although up to about 3 substituents per aromatic ring may be employed, it is often observed that steric effects reduce the acylation rate to an extent where acylation is impractical under reasonable reaction conditions. Consequently, monosubstitution and, to a lesser extent, disubstitution is more commonplace.

Of all the acylatable aromatic compounds which may be used in the practice of this invention the simplest one, benzene, is by far the most important because of its availability and because of its being the basis for more complex aryl ketones. Alkyl substituted benzenes generally also find particular importance in the practice of this invention.

The acylatable aromatic compound is reacted with an anhydride of a carboxylic acid. The anhydride generally is not a limitation in the practice of this invention, i.e., virtually any carboxylic acid anhydride may be used so long as it is stable under reaction conditions. Aromatic, aliphatic, cycloaliphatic, and heterocyclic anhydrides may be successfully employed in the practice of my invention. Among the aromatic carboxylic acids whose anhydrides may be used as the acylation agent are included such acids as benzoic acid, phthalic acid, naphthalene carboxylic acid, naphthalene dicarboxylic acid, and ring-substituted derivatives of benzoic acid. The latter include monosubstituted benzoic acids where the substituent is an alkyl, alkoxy, halogen, or nitro group. Generally the alkyl and alkoxy groups will contain from 1 up through 10 carbon atoms, and more likely will contain from 1 to about 6 carbon atoms. Examples include nitrobenzoic acids, methylbenzenecarboxylic acid, ethylbenzenecarboxylic acid, propylbenzenecarboxylic acid, dimethylbenzenecarboxylic acid, chlorobenzoic acid, chlorobromobenzoic acid, methylchlorobenzoic acid, methoxybenzoic acid, ethoxybenzoic acid, propoxybenzoic acid, chloromethoxybenzoic acid, and so forth.

Anhydrides from aliphatic carboxylic acids also may be used in this invention and include both fully saturated aliphatic carboxylic acids as well as unsaturated carboxylic acids containing from 2 up through about 20 carbon atoms. The anhydrides of both monocarboxylic acids and dicarboxylic acids may be used. Examples of suitable carboxylic acids include acetic acid, propionic acid, butyric acid, pentanoic acid, hexanoic acid, heptanoic acid, octanoic acid, nonanoic acid, decanoic acid, succinic acid, and glutaric acid. Examples of unsaturated acids whose anhydrides may be used in the practice of this invention include acrylic acid, crotonic acid, maleic acid, and so forth. The aliphatic carboxylic acids which may be used also may bear other substituents on the aliphatic chain so long as they do not substantially interfere with the acylation reaction. Cycloalkane carboxylic acids also form a subset of aliphatic carboxylic acids which may be successfully used. Among the more commonly used carboxylic acid anhydrides are included benzoic acid, ring-substituted benzoic acids, acetic acid, and other saturated aliphatic acids, both monocarboxylic and dicarboxylic acids, containing up through about 6 carbon atoms. Maleic acid is an outstanding example of a unsaturated carboxylic acid which may be employed in the practice of this invention.

The acylatable aromatic compound and the carboxylic acid anhydride are reacted, preferably in the liquid phase, in the presence of a solid acid catalyst. According to the reaction as exemplified below, $$C_6H_6 + (C_6H_5CO)_2O \rightarrow C_6H_5COC_6H_5 + C_6H_5COOH$$

the aromatic compound and the carboxylic acid anhydride react in equal molar proportions and afford as products equal molar amounts of the ketone and the carboxylic acid. The actual molar proportion of reactants used can be varied over a wide range so that the least expensive reactant is in excess. For example, where benzene is used as the aromatic compound to be acylated it may be used in large excess to ensure complete reaction of a relatively more expensive carboxylic acid anhydride. However, when the aromatic compound is the relatively more expensive reactant, as for example in the reaction of a chlorinated toluene with acetic anhydride, the anhydride may be employed in relatively large molar access to ensure complete reaction of the relatively more expensive aromatic hydrocarbon. Thus the range of molar proportion of reactants which may be used varies from about 25:1 or aromatic compound:anhydride through about 1:25 of aromatic compound:carboxylic acid anhydride. The exact proportions that are used is more a question of convenience and subjective judgment rather than any inherent limitation within our invention.

The acylatable aromatic hydrocarbon and the carboxylic acid anhydride are reacted over the solid acid catalysts of this invention. The latter include the silica-aluminas, especially those whose silica-alumina ratio varies between about 50:50 up to about 95:5. Ammonium fluorosilicate-treated silica-aluminas also function well in the practice of the invention. These are silica-aluminas which have been dealuminated with ammonium fluorosilicate as described in U.S. Pat. No. 5,008,233. The sulfated oxides of tungsten, zirconium, titanium, hafnium, niobium, tin, silicon and tantalum also serve as effective catalysts in our invention. These catalysts previously have been noted to have "super acid" characteristics and have been described in such publications as U.S. Pat. Nos. 4,956,519 and 4,406,821 as well as Japanese Public Disclosure 245854/89, all of which are hereby incorporated by reference. Particularly desirable are those catalysts which are sulfated oxides of zirconium, tungsten, or titanium.

Another class of catalysts which may be used in the practice of our invention are the pillared interlayered clays, often referred to by the acronym PILCs, and sometimes just referred to as pillared clays. Naturally occurring clays such as smectites, vermiculites and bentonites are composed of semicrystalline aluminosilicate layers (lamellae) held together by Van der Waals and electrostatic forces. Anionic charges on the siliceous layers are neutralized by cations in the interlamellar spaces. When these cations are large oligomers of inorganic cations such as $Fe^{+3}$ or $Cr^{+3}$, or when they are metal hydroxy polymer cations such as $[Al_{13}O_4(OH)_{24}(H_2O)_{12}]^{+7}$ or $[Zr(OH)_2 \cdot 4H_2O]_4^{8+}$, introduced during the preparation of the layered clays, the cations act as pillars, propping the clay layers apart to afford a pillared interlayered clay.

Pillared clays are characterized by having an interlamellar distance after drying at 150° C. of more than 5 angstroms and by having substantial microporosity, i.e., a micropore volume in the range of about 0.15–0.4 cc per gram where the micropore diameter was no more than about 20 Angstroms. Although small, non-oligomeric metal cations may occur in the interlamellar region of layered clays such materials are not pillared clays; upon heating such materials (to effect dehydration) the interlamellar space collapses because a small, unhydrated metal cation is unable to act as a pillar to hold apart adjacent layers. Such a collapse upon heating distinguishes metal-exchanged but non-pillared clays from pillared clays.

Examples of such materials include layered clays as montmorillonite which have as pillars oligomers of metal cations such as chromium and aluminum (U.S. Pat. No. 4,499,319), a hydrogen ion-exchanged pillared clay (U.S. Pat. No. 4,605,806), an oligomeric metal cation exchanged trioctahedral 2:1 layer-lattice smectite-type clay as disclosed in U.S. Pat. No. 3,965,043, and oligomeric metal cation-pillared synthetic hectorite-type clays taught in U.S. Pat. No. 3,979,331. Clays such as bentonite, montmorillonite, hectorite, saponite, and their synthetic analogs, may be modified by introducing pillars between the layers to give PILCs. Among the metal cations whose oligomers may be used are known iron (III), chromium (III), aluminum, titanium (IV), and zirconium (IV). Pillared clays whose pillars are aluminum chlorohydrate—a polymeric metal complex with the empirical fromula $Al_{2+n}(OH)_{2n}Cl_6$, where n has a value of about 4 to 12 (Tsuitida and Kobayashi, *J. Chem. Soc. Japan* (Pure Chem. Sect.), 64, 1268 (1943); Inoue, Osugi and Kanaji, *J. Chem. Soc. Japan* (Ind. Chem. Sec.) 61, 407 (1958)) are widely known and are referred to as ACH clays.

A rate earth aluminum chlorohydrate (ACH) is an ACH-pillared clay as described above which is modified to include one or more rare earth elements, i.e., elements of atomic number 57 through 71, such as cerium, lanthanum, neodymium, europium, samarium, praesodymiun, etc. The ACH polymer used in the preparation of the pillared clay is modified with the rare earth by adding a soluble rare earth salt, preferably a water soluble rare earth salt. Examples of rare earth salts are the nitrates, halides, sulfates and acetates. Preferred rare earth elements are cerium and lanthanum with cerium nitrate and lanthanum nitrate being the preferred salts. The rare earth is introduced into the polymer or oligomer structure by mixing the rare earth salt either in solution (water preferred) or as a solid with the ACH. The mixture is refluxed at a temperature of about 105° to about 145° C. for a time of about 24 to about 100 hours. The molar ratio of rare earth (expressed as oxide, e.g., $CeO_2$) to alumina ($Al_2O_3$) in the solution prior to refluxing is from about 1:52 to about 1:1.

When pillars of aluminum chlorohydrate containing one or more rare earths are introduced into the aforementioned clays (see U.S. Pat. No. 4,952,544), the resulting pillared clays are referred to as rare earth ACH PILCs, e.g., Ce-ACH PILC, La-ACH PILC, and so on. The ACH or rare earth ACH clays are prepared by means well known in the art such as adding the desired clay to an ACH or rare earth ACH solution, stirring, filtering, redispersing with water (one or more times), isolating, drying and calcining at about 500° to about 800° for a time sufficient to fix the structure (preferably about 3 hours). Any and all mixtures of the clays enumerated above can be used in the invention.

Typically acylations are performed in the liquid phase at temperatures between about 200° and 300° C. Reaction pressure is not an important variable except insofar as it ensures liquid phase conditions. Usually pressures of no greater than about 1500 psig suffice, where the pressure is effected by an inert gas such as nitrogen.

The reaction between the acylatable aromatic compound and the carboxylic acid anhydride may be effected either in a batch or, more preferably, in a continuous process. Where reaction occurs in a batch process, approximately 1 gram of catalyst per 0.01 mole of the limiting reactant, for example, anhydride, is sufficient. Either more or less catalyst may be used with the amount of catalyst affecting principally the rate of acylation rather than having any other profound effects on the reaction. Typically reaction will be effected by reacting from between 25 to about 0.04 molar proportions of acylatable or aromatic compound per mole of carboxylic acid anhydride at a temperature between about 200° and about 300° C. in the presence of the catalysts of this invention. Since this is a heterogeneous reaction, good mixing in the liquid phase is highly desirable. Reaction times will depend upon temperature and the reactivity of the various components but typically will lie between about 1 and about 10 hours.

In a continuous process the solid acid catalysts of this invention will be used typically as a packed bed with reactants passing through the reaction zone containing the packed bed of catalyst either in an upflow or a downflow mode. The reaction zone is held at a temperature between about 200° and about 300° C. with pressures therein sufficient to maintain the reactants in a liquid phase. The effluent from the reaction zone will contain the formed aromatic ketone, the carboxylic acid which is formed via acylation, and unreacted components, principally that component which was used in large excess in the reaction mixture entering the reaction zone. In those cases where an aromatic hydrocarbon is used in large excess, a quite desirable variant is possible where unreacted aromatic hydrocarbon is separated from the product mixture exiting the reaction zone and the separated aromatic compound is returned to the reaction zone. In another variant both the acylatable aromatic compound and the carboxylic acid present in the effluent from the reaction zone are separated, the carboxylic acid is separately converted to its anhydride, and the mixture of the anhydride and the acylatable aromatic compound is returned to the reaction zone. Other variants are of course possible and will be clear to those skilled in the art.

The examples which follow illustrate the claimed invention but are not intended to limit it in any way.

EXAMPLES 1-8

Representative Acylation

To an 850 mL glass liner for a rotating autoclave was charged appropriate amounts of benzoic acid anhydride, benzene, and catalyst. The liner was placed into a rotating autoclave, was flushed once with nitrogen and then charged to between 1,000-1,500 psig with nitrogen. The autoclave was heated to reaction temperature for 8 hours, after which it was cooled to ambient temperature and was vented slowly. The solid acid catalyst was removed by filtering the reaction product and the product was weighed and analyzed by gas liquid chromatography or high pressure liquid chromatography. Typical results are found in the accompanying table.

TABLE 1

ALKYLATION OF BENZENE WITH BENZOIC ANHYDRIDE TO PREPARE BENZOPHENONE

| Example | Benzene Moles | Benzoic Acid Anhydride Moles | Mole Ratio Benzene: Anhydride | Catalyst | Catalyst Amount | Temp °C. | Pressure PSIG/$N_2$ | Conversion of Anhydrides | Benzophenone Percent Formed | Selectivity[a] |
|---|---|---|---|---|---|---|---|---|---|---|
| 1 | 1 | 0.05 | 20:1 | 75:25 silica-alumina | 5 g | 300 | 1000 PSIG | 100.00 | 36.82 | 61.4 |
| 2 | 1 | 0.046 | 22:1 | 75:25 silica-alumina | 5 g | 300 | 1000 PSIG | 100.00 | 54.00 | 90.0 |
| 3 | 1 | 0.1 | 10:1 | 75:25 silica-alumina | 5 g | 300 | 1500 PSIG | 100.00 | 47.17 | 78.6 |
| 4 | 1 | 0.046 | 22:1 | 14% AFS Treated | 5 g | 300 | 1500 PSIG | 100.00 | 34.60 | 57.7 |
| 5 | 1 | 0.046 | 22:1 | Sulfated Zirconia | 5 g | 300 | 1500 PSIG | 100.00 | 5.90 | 9.8 |
| 6 | 1 | 0.046 | 22:1 | Ce—ACH PILC | 5 g | 300 | 1500 PSIG | 100.00 | 30.20 | 50.3 |
| 7 | 1 | 0.046 | 22:1 | Ce—ACH PILC | 3 g | 250 | 1500 PSIG | 85.73 | 54.82 | 91.4 |
| 8 | 1 | 0.046 | 22:1 | Fe+3/CLAY | 5 g | 200 | 1500 PSIG | 83.7 | 41.1 | 81.8 |

[a]Selectivity is here defined as: (benzophenone formed/theoretical maximum benzophenone) × 100

EXAMPLES 9-22

Additional Acylations

In a manner similar to that described above, other representative acylatable aromatic compounds may be reacted with representative carboxylic acid anhydrides. Among the representative aromatic compounds which may be acylated are toluene, anisole, chlorobenzene, xylene, naphthalene, and butoxybenzene. Among the representative carboxylic acids whose anhydrides may be employed are included phthalic acid, nitrobenzoic acid, methylbenzenecarboxylic acid, bromobenzenecarboxylic acid, cyclohexanecarboxylic acid, acetic acid, maleic acid, glutaric acid, and 1,2-cyclopentanecarboxylic acid. In each case appropriate amounts of the aromatic compound and the anhydride may be heated to a temperature from 200° C. to about 300° C. at sufficient pressure to afford a liquid phase reaction and, for survey purposes, may be kept at reaction temperature for 4-8 hours in the presence of a solid acid catalyst. The following table indicates the reactions which may be carried out in accord with my invention.

TABLE 2

Alkylation of Aromatic with Carboxylic Acid Anhydrides

| Example | Aromatic Compound | Anhydride[a] | Catalyst[b] |
|---|---|---|---|
| 9 | Benzene | nitrobenzoic | 90:10 silica:alumina |
| 10 | Benzene | methylbenzoic | sulfated titanium |
| 11 | Benzene | cyclohexane-carboxylic | ACH PILC |
| 12 | Toluene | bromobenzoic | La—ACH PILC |
| 13 | Toluene | acetic | sulfated zirconia |
| 14 | Anisole | acetic | ACH PILC |
| 15 | Xylene | acetic | 85:15 silica:alumina |
| 16 | Chlorobenzene | trifluorocetic | 85:15 silica:alumina |
| 17 | naphthalene | benzoic | Nd—ACH PILC |
| 18 | Butoxybenzene | benzoic | sulfated titania |
| 19 | Benzene | maleic | sulfated titania |
| 20 | Benzene | glutaric | 80:20 silica:alumina |
| 21 | Benzene | 1,2-cyclohexane-carboxylic | sulfated zirconia |
| 22 | Benzene | phthalic | sulfated zirconia |

[a]The names of the carboxylic acids are given in the table.
[b]Either in a batch reaction or a continuous process using a catalyst bed.

What is claimed is:

1. A method of preparing a ketone by acylation of an acylatable aromatic compound selected from the group consisting of aromatic hydrocarbons, hydroxy-substituted aromatic hydrocarbons, alkoxy-substituted aromatic hydrocarbons where the alkoxy group contains from 1 through 10 carbon atoms, and halogen-substituted aromatic hydrocarbons with a carboxylic acid anhydride comprising reacting at acylation conditions from about 25 to about 0.04 molar proportions of the acylatable aromatic compound with one molar proportion of a carboxylic acid anhydride in the presence of a catalyst selected from the group consisting of silica-aluminas containing from about 50 to about 95 weight percent silica, silicon-enhanced silica-aluminas, sulfated oxides of tungsten, hafnium, niobium, tantalum, silicon, tin, zirconium, and titanium, pillared clays, and rare earth aluminum chlorohydrate pillared clays, and recovering the ketone formed.

2. The method of claim 1 where the aromatic hydrocarbons are selected from the group consisting of benzene, naphthalene, anthracene, and alkyl-substituted benzenes, naphthalenes, and anthracenes, where each alkyl group contains from 1 through about 20 carbon atoms.

3. The method of claim 2 where the aromatic hydrocarbon is an alkyl-substituted benzene containing up to 3 alkyl groups on the aromatic ring and where each alkyl group contains from 1 up through 10 carbon atoms.

4. The method of claim 3 where the aromatic hydrocarbon is an alkyl-substituted benzene containing 1 or 2 alkyl groups, each of which contains from 1 to 6 carbon atoms.

5. The method of claim 1 where the carboxylic acid anhydride is an aromatic carboxylic acid anhydride.

6. The method of claim 1 where the carboxylic acid anhydride is a heterocyclic carboxylic acid anhydride.

7. The method of claim 1 where the carboxylic acid anhydride is an aliphatic carboxylic acid anhydride and where the aliphatic carboxylic acid is a monocarboxylic acid or a dicarboxylic acid containing from 2 up through about 20 carbon atoms.

8. The method of claim 7 where the carboxylic acid of the anhydride contains from 2 up through about 10 carbon atoms.

9. The method of claim 1 where the catalyst is a sulfated oxide of zirconium, tungsten, or titanium.

10. The method of claim 1 where the catalyst is a pillared clay selected from the group consisting of a montmorillonite, a bentonite, a saponite, or a hectorite clay having pillars selected from the group consisting of oligomeric cations of aluminum, zirconium, chromium, iron, and titanium.

11. The method of claim 1 where the catalyst is a rare earth aluminum chlorohydrate pillared clay selected from the group consisting of Ce-ACH PILC and La-ACH PILC.

12. The method of claim 1 where acylation conditions include a temperature from about 200° to about 300° C. and a pressure sufficient to ensure a liquid phase reaction.

13. A method of continuous preparation of a ketone comprising reacting in a reaction zone at acylation conditions an excess of an acylatable aromatic compound selected from the group consisting of aromatic hydrocarbons, hydroxy-substituted aromatic hydrocarbons, alkoxy-substituted aromatic hydrocarbons where the alkoxy group contains from 1 through 10 carbon atoms, and halogen-substituted aromatic hydrocarbons with a carboxylic acid anhydride in the presence of a bed of a catalyst selected from the group consisting of silica-aluminas containing from about 50 to about 95 weight percent silica, silicon-enhanced silica-aluminas, sulfated oxides of tungsten, hafnium, niobium, tantalum, zirconium, tin, silicon, and titanium, pillared clays, and rare earth aluminum chlorohydrate pillared clays, to afford a product mixture containing ketone, carboxylic acid, and unreacted acylatable aromatic compound, separating the acylatable aromatic compound from at least the ketone, and returning the separated acylatable aromatic compound to the reaction zone.

14. The method of claim 13 where the aromatic hydrocarbons are selected from the group consisting of benzene, naphthalene, anthracene, and alkyl-substituted benzenes, naphthalenes, and anthracenes, where each alkyl group contains from 1 through about 20 carbon atoms.

15. The method of claim 14 where the aromatic hydrocarbon is an alkyl-substituted benzene containing up to 3 alkyl groups on the aromatic ring and where each alkyl group contains from 1 up through 10 carbon atoms.

16. The method of claim 15 where the aromatic hydrocarbon is an alkyl-substituted benzene containing 1 or 2 alkyl groups, each of which contains from 1 to 6 carbon atoms.

17. The method of claim 13 where the carboxylic acid anhydride is an aromatic carboxylic acid anhydride.

18. The method of claim 13 where the carboxylic acid anhydride is an aliphatic carboxylic acid anhydride and where the aliphatic carboxylic acid is a monocarboxylic acid or a dicarboxylic acid containing from 2 up through about 20 carbon atoms.

19. The method of claim 14 where the carboxylic acid of the anhydride contains from 2 up through about 10 carbon atoms.

20. The method of claim 13 where the catalyst is a sulfated oxide of zirconium, tungsten, or titanium.

21. The method of claim 13 where the catalyst is a pillared clay selected from the group consisting of a montmorillonite, a bentonite, a saponite, or a hectorite clay having pillars selected from the group consisting of oligomeric cations of aluminum, zirconium, chromium, iron, and titanium.

22. The method of claim 13 where the catalyst is a rare earth aluminum chlorohydrate pillared clay selected from the group consisting of Ce-ACH PILC and La-ACH PILC.

23. The method of claim 13 further characterized in that in the product mixture the acylatable aromatic compound and carboxylic acid are separated from the formed ketone, the carboxylic acid is converted to the corresponding carboxylic acid anhydride, and a mixture of the unreacted acylatable aromatic compound and the carboxylic acid anhydride is returned to the reaction zone.

24. The method of claim 13 where the carboxylic acid anhydride is a heterocyclic carboxylic acid anhydride.

* * * * *